(12) United States Patent
Willard, III

(10) Patent No.: US 7,754,146 B2
(45) Date of Patent: Jul. 13, 2010

(54) FIELD TEST KIT FOR THE DETECTION OF MONOSODIUM GLUTAMATE (MSG) IN FOOD STUFFS AND DRINKS

(76) Inventor: George Fredrick Willard, III, 2029 Fall Haven La., Knoxville, TN (US) 37932

( * ) Notice: Subject to any disclaimer, the term of this patent is extended or adjusted under 35 U.S.C. 154(b) by 1002 days.

(21) Appl. No.: 11/503,884

(22) Filed: Aug. 15, 2006

(65) Prior Publication Data
US 2008/0032008 A1     Feb. 7, 2008

(51) Int. Cl.
*B01L 3/00*     (2006.01)
(52) U.S. Cl. .................. 422/61; 422/99; 422/102; 436/815
(58) Field of Classification Search ............... 422/61, 422/99, 102; 436/815
See application file for complete search history.

(56) References Cited

U.S. PATENT DOCUMENTS

| | | | | |
|---|---|---|---|---|
| 1,865,472 | A | * | 7/1932 | Lamstein .................. 219/385 |
| 4,073,623 | A | * | 2/1978 | Bodart ....................... 422/55 |
| 5,824,554 | A | | 10/1998 | McKay |
| 6,417,498 | B1 | * | 7/2002 | Shields et al. ............... 219/521 |

* cited by examiner

*Primary Examiner*—Jill Warden
*Assistant Examiner*—M. T. Cole

(57) ABSTRACT

The present invention is directed to field test kits, methods, and compositions for the field detection of monosodium glutamate (MSG) and related materials in foodstuffs and drinks. The field test kit consists of a reaction chamber, a closed reaction vessel containing encapsulated chemicals, and a means of providing heat to the reaction chamber, all housed in a convenient construction. The function of the encapsulated chemicals is to produce a colorimetric reaction with MSG at very low concentrations.

14 Claims, 1 Drawing Sheet

FIELD TEST KIT FOR THE DETECTION OF MONOSODIUM GLUTAMATE (MSG) IN FOOD STUFFS AND DRINKS

FIELD OF THE INVENTION

The present invention relates to the rapid and convenient determination of the presence of monosodium glutamate (MSG) and related compounds in foodstuffs and drinks in a non-laboratory environment.

BACKGROUND OF THE INVENTION

Glutamic acid, also known as α-aminoglutaric acid or 2-amino pentanedioc acid, is a nonessential amino acid with the chemical formula COOH(CH2)2CH(NH2)COOH (FW=147.13 g, CAS No. 56-86-0). The naturally occurring form is the L(+)-glutamic acid (mp=205° C. with decomposition). It is usually found in foodstuffs and drinks as the sodium salt, monosodium glutamate, also known as sodium glutamate or MSG, with the chemical formula COOH(CH2)2CH(NH2)COONa (FW=187.14 g, CAS No. 6106-04-3). MSG (mp=232° C. with decomposition). MSG is used as a flavor enhancer in foodstuffs and drinks at about 0.3%.

Many people have an allergic or adverse reaction to MSG in food. Symptoms vary in type and magnitude but can include rashes and swelling of the throat. Tolerance levels vary person to person but sensitive people can react to 5 g of MSG, whereas non-sensitive people can tolerate up to 25 g. MSG is found in more than Chinese cooking. It occurs naturally in parmesan cheese, tomatoes, spinach, mushrooms, and seaweed. It is also in tuna and some ice creams. The issue is that it is also hidden in foods as a flavor enhancer. If you are Type II diabetic, then the MSG can raise your blood pressure. MSG is especially bad for anyone with Renal Failure (kidney failure).

MSG is known as monosodium glutamate, glutamate, glutamic acid, Accent®, Ajinomoto®, hydrolyzed oat flour, Glutavene®, and L-cysteine. MSG is almost always present in glutamate, yeast extract, hydrolyzed protein, glutamic acid, calcium caseinate, sodium caseinate, yeast food, gelatin, textured protein, yeast nutrient, and autolyzed yeast. MSG is often found in natural beef flavorings, stock, broth, malt extract, soy sauce, and soy protein. So although a chef might not deliberately add MSG to his cuisine, it may be added accidentally in a broth or other ingredient.

Since it is very difficult to determine what foodstuffs might actually contain MSG, there is a strong need for a field test kit that can determine the presence of MSG in foodstuffs and drinks quickly and efficiently in a non-laboratory environment such as a restaurant or other dining establishment.

A survey of the literature indicated very few chemical systems that would be appropriate to use in the present invention. It was decided that a colorimetric change would be required for an inexperienced person to determine a positive reaction to MSG. A spot reaction test was found that was reported to be effective at very low levels of an alpha-amino acid.[1]

This spot test method involves the detection of an α-amino acid through condensation with pyridine-2-aldehyde to form a Schiff base (an imine). Pyridine is used to ensure the availability of the amino group for reaction by neutralization of the carboxylic acid group. Cobalt nitrate is used as a chelating agent to give a colored species that can be visually determined. This method requires mixing a reagent and then heating the reagent with the sample for one to three minutes.

There is no reported data regarding the reaction with MSG. However, the method is very sensitive to α-amino acids. The following materials tested positive: 3 γ cystine, 3 γ cysetine, 2.5 γ methionine, 5 γα-alanine, 2 γ lysine, 1 γ glycine, 3 γ tyrosine, 1 γ L-leucine, 5 γ aspartic acid, and 5 γ asparagine. A positive response was also obtained for monoiodo-L-tyrosine, valine, citrulline, arginine, phenylalanine, tryptophan, and 2-amino-n-octanoic acid.

The issue with the reagents selected for the colorimetric reaction is the short shelf-life once the reagent is prepared by mixing the pyridine-2-aldehyde solution and the cobalt nitrate solution. It is reported that the shelf life is only one week which would make this system unacceptable for a field test kit.

In U.S. Pat. No. 5,824,554 a dining mat, such as a doily, composed of absorbent material and small spots of applied reagents was used to determine the presence of allergenic substances.[2] In use, food is applied to the reagents on the dining mat, and the reagent changes its appearance indicating the presence of the allergenic substance in the food product. The advantage of this method is that only a small sample of food is required and the food is not contaminated by the testing. However, although MSG was listed as an allergenic material, there was no mention of any reagent system that might allow for the detection of MSG in the food. Since the spot test requires the use of a liquid reagent, namely pyridine-2-aldehyde, this dining mat method using the reagents of the spot test method will not work for MSG. At best, the dining mat method will suffer the same short shelf-life issue as the mixture of reagents from the spot test.

Therefore, a solution to this shelf-life issue is provided by this invention while maintaining the advantages of convenience of use and no food contamination found in the prior art. An encapsulating material is needed to keep the reactive chemicals separate until they are required to react with the foodstuff. Since the colorimetric reaction occurs at near boiling water temperature, it is desirable to have this encapsulating material melt below that temperature. It has been surprisingly found that a low melting paraffin wax can function as an encapsulating material.

SUMMARY OF THE INVENTION

The present invention is directed to field test kits, methods, and compositions for the field detection of monosodium glutamate (MSG) and related materials in foodstuffs and drinks. The field test kit 10 is small enough for someone to carry the device in a jacket pocket or purse. It is simple, safe, and convenient to use in a public area such as a restaurant or other dining establishment. The field test kit 10 consists of a reaction chamber 12, a closed reaction vessel 14 containing encapsulated chemicals 16, and a means of providing heat to the reaction chamber 12, all housed in a convenient construction 36. The reaction chamber 12 consists of a tube which is the correct size to hold the reaction vessel 14. The closed reaction vessel 14 can be a glass vial 22 with a plastic cap 24. In order to use the reaction vessel 14, the plastic cap 24 is removed, a small sample of the test food 34 is inserted into the reaction vessel 14 using a fork, spoon, or straw, and the plastic cap 24 is replaced. The function of the encapsulated chemicals 16 is to produce a colorimetric reaction with MSG at very low concentrations. The present invention comprises heating the reaction chamber 12 electrically using a nichrome wire 20, a battery pack 26, a switch 32, and an LED indicator 30. Enough turns of nichrome wire 20 are applied to the reaction chamber 12 to produce a temperature of about 200° F. in the reaction vessel 14. Materials of the housing construction 36 include plastics.

DESCRIPTION OF THE DRAWING

A front view of the invention is shown in FIG. 1. The field test kit 10 consists of there basic elements of a reaction chamber 12, a closed reaction vessel 14 containing encapsulated chemicals 16 and 18, and a means of providing heat to the reaction chamber 12, all housed in a convenient construction 36. An electrical circuit consisting of a battery pack 26 with AA batteries 28, nichrome wire 20 wrapped around the reaction chamber 12 which in turn provides heat to the closed reaction vessel 14. The closed reaction vessel 14 typically consists of a glass vial 12 with a plastic cap into which a sample of food 34 can be placed for testing.

DETAILED DESCRIPTION OF THE INVENTION

Figure 1:
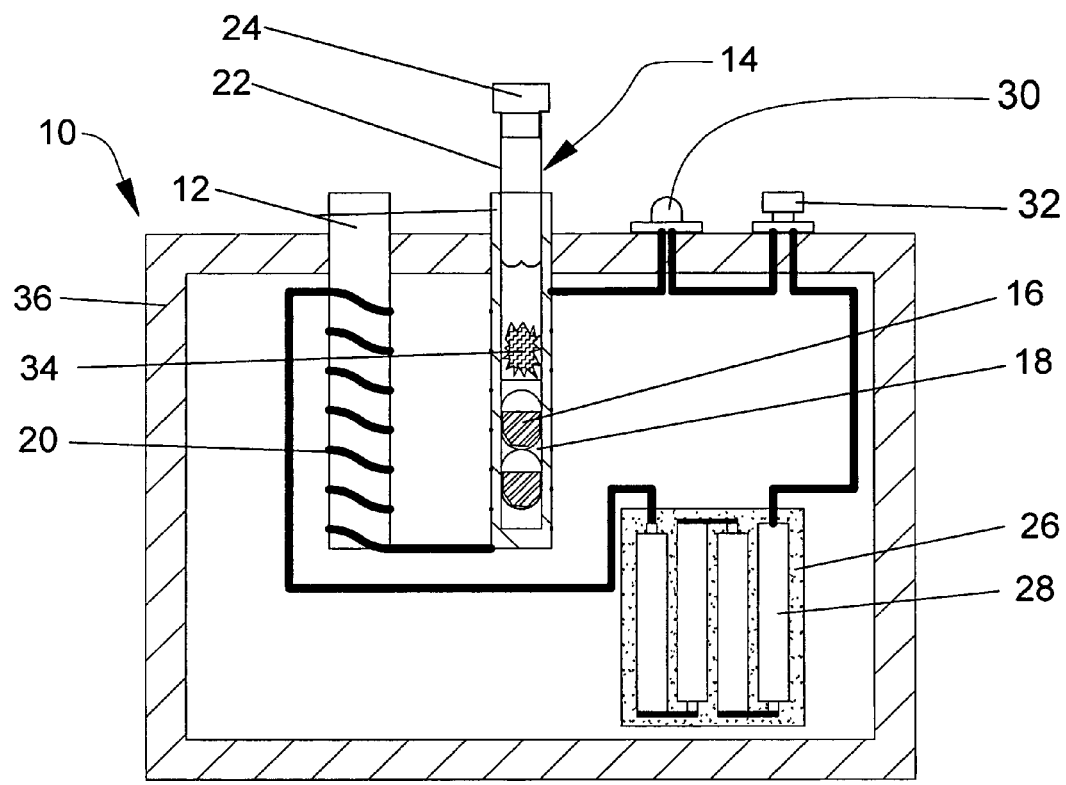

The present invention comprises a field test kit 10 for detecting the presence of monosodium glutamate (MSG) in foodstuffs and drinks. The field test kit 10 comprises a reaction chamber 12, a closed reaction vessel 14 containing encapsulated chemicals 16, and a means of providing heat to the reaction chamber 12, all housed in a convenient construction 36. The construction 36 is made of plastic such that there are three compartments. The reaction chamber 12 housed in the top compartment comprises a brass tube about 0.5 inches in diameter and about one inch in length insulated with polyester film and wrapped with eight turns of 21-gauge nichrome wire 20. The closed reaction vessel 14 containing encapsulated chemicals 16 comprises a 2 ml glass vial 22 with a plastic cap 24 with a center section of silicone. The encapsulated chemicals 16 consist of an aqueous solution of 2-pyridine-carboxyaldehyde and sodium hydroxide and separately an aqueous solution of cobalt nitrate. The encapsulating material 18 is a low melting paraffin wax (mp 120° F.). In order to use the reaction vessel 14, one reaction vessel 14 is removed from the bottom storage compartment, the plastic cap 24 is removed; a very small sample of the test food 34 is inserted into the reaction vessel 14 using a fork, spoon, or straw; and the plastic cap 24 is replaced. The reaction vessel 14 is then placed in the reaction chamber 12 such that the plastic cap 24 extends above the top compartment of the housing so as to allow easy removal. The encapsulated chemicals 16 react with the MSG in the test food 34 when heated for up to three minutes to produce a colorimetric change which can be observed visually as a change from yellow to dark red or blue once the reaction vessel 14 is removed from the reaction chamber 12. The reaction chamber 12 is heated electrically by applying a current to a nichrome wire 20 wrapped around the brass tube using a battery pack 26 of four AA batteries 28 found in the middle compartment and a push switch 32 and an LED 30 protruding from the top compartment on the right hand side. The reaction vessel 14 reaches about 200° F. in about two to three minutes causing the encapsulating material 18, such as wax, to melt and allowing the encapsulated chemicals 16 to mix and react with the test food 34 sample containing MSG. The reaction vessel 14 can be removed temporarily and shaken to increase mixing. A positive test is a color change from yellow to dark red or blue. After the test is complete, the reaction vessel 14 is placed on a level surface and allowed to cool to room temperature. The encapsulating material 18, such as wax, floats to the surface of the reaction vessel 14 due to its lower density as it cools and solidifies forming a barrier on the surface. Thus, the chemicals contained therein are protected from human contact, making disposal convenient and safe.

In one embodiment, the present invention provides a method for determining the presence of MSG in foodstuffs and drinks comprising the steps of: removing a reaction vessel 14 from the storage compartment of the field test kit housing construction 36; opening the reaction vessel 14 by removing the cap 24 and then introducing a small food sample 34 into a reaction vessel 14 containing encapsulated chemicals 16; closing the reaction vessel 14 and placing the reaction vessel 14 in a reaction chamber 12; heating the reaction chamber 12 to about 200° F. for 1 to 3 minutes; and visually observing the color change in the reaction vessel 14. The color change is usually from yellow to a deep red or purple.

In one embodiment of the housing construction 36, the housing is constructed of polystyrene panels into three compartments consisting of a bottom storage compartment for reaction vessels 14; a middle compartment holding 4 AA batteries 28; a top compartment containing the reaction chamber 14, push-button switch 32, and a light-emitting diode 30, and a cover door allowing access to the middle and bottom compartments.

In another embodiment of the housing construction 36, ABS plastic is used in place of polystyrene to build the three compartments.

In another embodiment of the housing construction 36, polycarbonate plastic is used in place of the polystyrene to build the three compartments.

In another embodiment of the housing construction 36, the 4 AA batteries 28 are replaced with a rechargeable 6-volt battery pack.

In another embodiment of the housing construction 36, the panels used to construct the three compartments can be replaced with an injection molded structure.

In another embodiment of the housing construction 36, the push-button switch 32 is replaced with a push-and-hold switch which would close the circuit for 1 to 3 minutes.

In one embodiment of the reaction chamber 12, a metal tube is used to provide a holder for the reaction vessel 14. The reaction chamber 12 needs to fit the reaction vessel 14 snuggly so as to be able to transfer heat efficiently. It was found that a 0.5 inch (outside diameter) brass tube fitted perfectly. About a one inch long piece was sufficient to cover the glass portion of the reaction vessel 14 (glass vial 22) and allow the cap 24 to protrude out of the heated area. However, the nichrome wire 20 cannot come into direct contact with an electrical conductor. Otherwise, the desired reaction chamber 12 temperature is not achieved. Hence, the exterior of the brass tube was electrically insulated with polyester film.

In another embodiment of reaction chamber 12, a ceramic tube is used to provide a holder for the reaction vessel 14. The reaction chamber 12 needs to fit the reaction vessel 14 snuggly so as to be able to transfer heat efficiently. The advantage of a ceramic tube over a metal tube is that the ceramic tube is not electrically conducting and the nichrome wire 20 used for heating can be incorporated directly into the ceramic tube.

In one embodiment of the reaction vessel 14, a clear glass vial 22 about 2 ml in volume is used. The vial 22 contains encapsulated chemicals 16 consisting of an aqueous solution of 2-pyridine-carboxyaldehyde and a base such as sodium hydroxide and separately an aqueous solution of cobalt nitrate.

In another embodiment of the reaction vessel 14, the vial 22 contains encapsulated chemicals 16 consisting of an aqueous solution of 2-pyridine-carboxyaldehyde and separately an aqueous solution of cobalt nitrate and a base such as pyridine.

In another embodiment of the reaction vessel 14, the vial 22 contains encapsulated chemicals 16 consisting of an aqueous solution of 2-pyridine-carboxyaldehyde and pyridine and separately an aqueous solution of cobalt nitrate.

In another embodiment of the reaction vessel 14, the vial 22 contains encapsulated chemicals 16 consisting of an aqueous solution of 2-pyridine-carboxaldehyde and sodium hydroxide solution and separately an aqueous solution of cobalt nitrate.

In another embodiment of the reaction vessel 14, the encapsulated cobalt nitrate is replaced with any water soluble cobalt salt such as cobaltous acetate, cobaltous ammonium sulfate, cobaltous bromide, cobaltous chloride, cobaltous iodide, or cobaltous sulfate.

In another embodiment of the reaction vessel 14, the glass vial 22 contains encapsulated chemicals 16 consisting of an aqueous solution of 2-pyridine-carboxaldehyde and sodium hydroxide solution and separately cobalt nitrate powder.

In another embodiment of the reaction vessel 14, the encapsulated chemicals 16 are prepared by surrounding each individual chemical mixture with an encapsulating material 18 consisting of a low melting and water insoluble material such as paraffin wax with a melting point of less than about 200° F. The paraffin wax does not react with the encapsulated chemicals 16. The reaction vessel 14 is first coated with a thin layer of paraffin wax by melting the wax and adding the molten wax to the reaction vessel 14 and allowing the wax to cool in contact with the walls and bottom of the reaction vessel 14 while the reaction vessel 14 is maneuvered so as to coat all the inner surfaces of the reaction vessel 14. Then the required amount of the first chemical mixture consisting, for example, of an aqueous solution of 2-pyridine-carboxaldehyde and a base such as sodium hydroxide is added. Then more molten wax is added to the reaction vessel 14 to seal this chemical mixture entirely. Thus, the first chemical mixture is fully encapsulated in the bottom of the reaction vessel 14. Next the second chemical mixture consisting, for example, of aqueous cobalt nitrate, is added to the reaction vessel 14. More molten wax is added to the reaction vessel 14 to seal this second chemical mixture entirely. Thus, the second chemical mixture is fully encapsulated on top of the first encapsulated chemical mixture. Therefore, the two chemical mixtures are kept separate in the reaction vessel 14 and not allowed to react. The cap 24 is then added to close the reaction vessel 14.

In another embodiment of the reaction vessel 14, the encapsulated chemicals 16 are prepared by containing each individual chemical mixture within a thin glass ampoule. The thin glass ampoule can be of any shape including a tube such as a melting point tube. For example, a chemical mixture of an aqueous solution of 2-pyridine-carboxaldehyde and a base such as sodium hydroxide is placed in a glass ampoule and sealed. Similarly, for example, aqueous cobalt nitrate is placed in a glass ampoule and sealed. One ampoule of each chemical mixture is then added to one reaction vessel 14 comprising a clear plastic vial. After addition of the test food 34 and sealing with the cap 24, the ampoules are broken by flexing the reaction vessel 14 so as to bend the ampoules causing them to rupture. Therefore, the two chemical mixtures are kept separate in the reaction vessel 14 and not allowed to react until needed for the test.

In one embodiment of the reaction chamber 12, nichrome wire 20 is used to heat a brass tube using an electrical circuit consisting of a battery pack 26, a push-button switch 32, and an LED indicator 30. The nichrome wire 20 is insulated from the brass tube using polyester film.

In another embodiment of the reaction chamber 12, the nichrome wire 20 is insulated from the brass tube with parchment paper.

In another embodiment of the reaction chamber 12, a ceramic tube can be used in place of the brass tube. The nichrome wire 20 can be embedded directly into the ceramic before it is thermally cured.

In another embodiment of the reaction chamber 12, other heat sources are used to heat the reaction vessel 14. In the absence of a complete field test kit 10, there are other options for heating the reaction vessel 14. One option is to hold the reaction vessel 14 under a stream of hot water. Another option is to place the reaction vessel 14 into a container of near boiling liquid such as water, hot coffee, or tea. Another option is to heat the reaction vessel 14 with hot air such as using a hair dryer. Another option is to heat the reaction vessel 14 with an open flame such as using a cigarette lighter. Another option is to use microwave radiation to heat the reaction vessel 14. It may take longer for the chemical reaction to occur using alternative heat sources, but the end result will be the same as if the reaction vessel 14 was electrically heated.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: CAS (Chemical Abstracts Service), cc (cubic centimeter), M (molar), g (grams), MSG (monosodium glutamate, glutamic acid, and any other form that this chemical may take), % (percentage), ml (milliliter), mg (milligram), MP (melting point), FP (freezing point), α (alpha), FW (formula weight), sec (seconds), ° F. (degrees Fahrenheit), ° C. (degrees Celsius), γ (microgram), LED (light emitting diode), and BP (boiling point).

2-pyridine-carboxyaldehyde ($C_6H_5NO$, FW=107.11, CAS No. 1121-60-4) is available from Aldrich Chemical. This liquid has a FP of 54° C. and a BP of 178-181° C. The density is 1.121 g/cc. It is soluble in water.

Cobalt nitrate is available as a hexahydrate from Aldrich Chemical (FW=291.03 g, CAS No. 10026-22-9). This solid has a MP of 56° C. and is soluble in water.

Example 1

Selection of Chemicals for Colorimetric Reaction with MSG

A solution of pyridine-2-aldehyde (FW=107.11 g, CAS No. 11221-60-4) was prepared in water at 0.5% concentration by dissolving 0.05 g of pyridine-2-aldehyde in 10 ml deionized water. A 0.1 M solution of cobalt nitrate was prepared by dissolving 0.291 g of cobalt nitrate hexahydrate (FW=291.03 g, CAS No. 10026-22-9) in 10 ml deionized water. A reagent was made by mixing five drops of the pyridine-2-aldehyde solution with one drop of the cobalt nitrate solution into a 10 ml glass test tube. To this mixture was added one drop of pyridine to ensure that the amino group of the alpha-amino acid was free to react. A test sample (only about 0.5 mg of material) of an alpha-amino acid (or other material) was then added to the test tube. If the sample was very dry, a few drops of water were also added. The test tube was capped with a plastic cap and heated in nearly boiling water for three minutes. A color change was indicative of the presence of an α-amino acid. The color change can vary from a yellow to a deep red to a deep violet. Table 1 gives the test results for several test samples. A 0.039 M standard solution was made of MSG (FW=187.14 g) by dissolving 0.066 g of MSG technical grade in deionized water.

TABLE 1

Test Results From Boiling Water

| Test No. | Test Material | Drops of Reagent/Drops of Pyridine | Resulting Color | Test Result |
|---|---|---|---|---|
| 1 | MSG, technical grade | 1/1 | Light purple | Positive |
| 2 | MSG, technical grade | 2/2 | Dark blue | Positive |
| 3 | MSG, technical grade Standard solution (2 drops) | 2/2 | Medium blue | Positive |
| 4 | Beef and Gravy Baby Food | 2/2 | Purple | Positive |
| 5 | Water | 2/2 | Yellow | Negative |
| 6 | Starch | 2/2 | Yellow | Negative |
| 7 | Aspartame | 2/2 | Light yellow | Negative |
| 8 | Yellow Mustard | 2/2 | Yellow | Negative |
| 9 | Canned Chicken | 2/2 | Clear | Negative |
| 10 | MSG, technical grade Standard solution (2 drops) | 2/2 | Purple | Positive |

The test method appears to be specific for MSG. A protein or peptide does not interfere.

Example 2

Encapsulating the Reagents in the Reaction Vessel 14

Paraffin wax such as that used for canning and candle making was chosen. The paraffin wax was melted in a pan over hot water. The melt temperature was measured to be about 160° F. using an IR thermometer. A few drops of the molten wax was transferred to a 2 ml glass vial 22 and allowed to coat the vial 22 on the bottom and midway up the sides as the wax cooled while the vial 22 was rotated. Five drops of the pyridine-2-aldehyde reagent solution was placed in the 2 ml glass vial 22. A few drops of molten wax were used to encapsulate this first reagent solution. Similarly, two drops of the cobalt nitrate reagent solution and two drops of pyridine were transferred to the vial. Then a few drops of molten wax were added. The wax was allowed to cool and encapsulate this second reagent solution. The vial 22 was closed with a plastic cap 24 with a silicone seal. After many weeks storage at room temperature, the layers were still separate.

In a separate experiment a low temperature paraffin wax (128° F.) was used as the encapsulating material 18. This paraffin wax was melted in a pan over hot water. The temperature of the melted wax was measured to be about 170° F. using an IR thermometer. A few drops (about 0.5 ml) of the molten wax was transferred to a 2 ml glass vial 22 and allowed to coat the vial 22 on the bottom and midway up the sides as the wax cooled while the vial 22 was rotated. Five drops of the pyridine-2-aldehyde reagent solution were placed in the 2 ml glass vial 22 along with 1 drop of 0.2 M sodium hydroxide solution. About ten drops of molten wax were used to encapsulate this first reagent solution. Similarly, three drops of the cobalt nitrate reagent solution were transferred to the vial 22. Then about ten drops of molten wax were added. The wax was allowed to cool and encapsulate this second reagent solution. It was noted that the wax in the heating pan began to solidify at about 128° F. After storage for over three months at room temperature, the layers in the vials were still separate.

Example 3

Selection of Materials for Reaction Chamber 12

Since the concept is to construct a small device that will fit into a purse or pocket, a 2 ml clear glass vial 22 with rubber septum cap 24 was chosen as the reaction vessel 14 due to its small size and easy access. Therefore, the reaction chamber 12 needs to fit this vial 22 snuggly so as to be able to transfer heat efficiently. It was found that a 0.5 inch (outside diameter) brass tube fitted perfectly. About a one inch long piece was sufficient to cover the glass portion of the vial 22 and allow the cap 24 to protrude out of the heated area. However, the nichrome wire 20 cannot come into direct contact with an electrical conductor. Otherwise, the desired reaction chamber 12 temperature is not achieved. Hence, the exterior of the brass tube was electrically insulated with polyester film. Other suitable materials include paper or ceramic.

Other materials were evaluated for construction of the reaction chamber 12 and were also found to be acceptable including aluminum foil molded around the glass vial 22. Also, a ceramic material was cast around the vial 22 with nichrome wire 20 present. The ceramic (about 0.125 inches thick) was cured by heating in an oven at 275° F. for 15 minutes.

Example 4

Selection of Heating Source for Reaction Chamber 12

The objective was to heat the reaction chamber 12 to about 200° F. to allow the wax to melt and allow the individual reactive ingredients to mix with the food sample 34. It was found that about 8 wraps of 21-gauge (0.0285 inch diameter) nichrome wire 20 (about 13 inches including leads) could supply the desired heat when powered by four AA batteries 28 as shown in Table 2. A brass reaction chamber 12 with polyester film insulation was used. A 2 ml clear glass vial 22 with an encapsulated chemical 16 of five drops of pyridine-2-aldehyde solution and an encapsulated chemical 16 of one drop of cobalt nitrate solution with one drop of pyridine was used as the reaction vessel 14. Two drops of the standard MSG solution were added and the vial 22 was sealed with a plastic cap 24 with a rubber septum center. The push-button switch 32 activated the heating circuit as indicated by the glowing LED 30. The temperature of the reaction chamber 12 was measured with an IR thermometer versus time as recorded in Table 2.

TABLE 2

Heating Rate Study

| Time (sec) | Temperature (° F.) |
|---|---|
| 0 | 82 |
| 10 | 120 |
| 20 | 134 |
| 30 | 150 |
| 60 | 160 |
| 75 | 179 |
| 90 | 182 |
| 120 | 196 |
| 150 | 209 |
| 180 | 211 |

The wax began to melt at about 150° F. and continued to melt as the temperature increased allowing mixing of the reagents with the sample. The rubber septum in the plastic cap 24 bulged slightly indicating that the sample was getting warm. The color change was from yellow to a medium red.

Example 5

Construction of Housing to Hold Components of Field Test Kit 10

Polystyrene sheets were cut to form a box with internal dimensions of about 3.5 inches wide by 3 inches tall by 1.5 inches deep. Three compartments were constructed by adding a shelf at one inch from the bottom and a shelf at one inch down from the top. The top compartment housed the reaction chamber 12 such that the 2 ml clear glass vial cap 24 sticks out a hole in the housing 36 above the brass tube which is centered in the left side of the compartment. The brass tube was insulated with polyester film. Next to this hole with the vial cap 24 protruding on the top side of the top compartment was placed a light emitting diode 30. Also, a push-button switch 32 was allowed to protrude out the top compartment on the right side of the housing 36. The center compartment housed a four pack 26 of AA batteries 28 equipped with a 9 volt battery terminal. The batteries 28 were wired through the switch 32 to the nichrome wire 20 on the reaction chamber 12. The bottom compartment served as a storage compartment for the reaction vessels 14 (2 ml glass vials 22 containing the encapsulated chemicals 16). This bottom compartment also serves to hold used vials 22. The top compartment was sealed off to prevent anyone touching the hot reaction chamber 12 or the wires to the switch 32 and LED 30. However, the bottom two compartments were accessible through a hinged door with clasp or a sliding door so as to allow removal and replacement of batteries 28 and reaction vessels 14.

From the above Examples, it is clear that the present invention represents a convenient and inexpensive method for the field testing of foodstuffs and drinks for the presence of MSG.

In summary, the present field test kit invention provides a novel approach to field testing for the presence of MSG in foodstuffs and drinks. Advantages of this invention include: (1) convenience of handling, (2) fast registration of results, (3) easy interpretation of results, and (4) a boon to public health.

REFERENCES CITED

1. F. Feigl, Vinzenz Anger, and R. E. Oesper, "Spot Test in Organic Analysis", Elsevier Scientific Publishing Company, New York, 1966, p. 370.

2. F. M. McKay, "Detection of allergenic substances in food products", U.S. Pat. No. 5,824,554 (Oct. 20, 1998).

What is claimed is:

1. A field test kit for detecting the presence of monosodium glutamate (MSG) and related materials in foodstuffs and drinks, wherein said kit comprises a reaction chamber having an internal void adapted to receive a closed reaction vessel, a closed reaction vessel containing encapsulated chemicals, and a means of providing heat to the reaction chamber, wherein said encapsulated chemicals comprise a base with pyridine-2-aldehyde and cobalt nitrate.

2. The field test kit of claim 1 wherein the reaction chamber is a tube.

3. The field test kit of claim 2 wherein the tube is electrically insulated metal.

4. The field test kit of claim 2 wherein the tube is ceramic.

5. A closed reaction vessel comprising a glass vial with a plastic cap containing encapsulated chemicals, wherein said encapsulated chemicals comprise a base with pyridine-2-aldehyde and cobalt nitrate.

6. The closed reaction vessel of claim 5 wherein the encapsulated chemicals comprise encapsulated base with pyridine-2-aldehyde and separately encapsulated aqueous cobalt nitrate.

7. The closed reaction vessel of claim 5 wherein the encapsulated chemicals comprise encapsulated base with pyridine-2-aldehyde and separately encapsulated cobalt nitrate powder.

8. The field test of claim 1 wherein an encapsulating material is used to encapsulate the chemicals individually in the reaction vessel.

9. The field test kit of claim 8 wherein the encapsulating material is low melting, water insoluble material.

10. The field test kit of claim 8 wherein the encapsulating material is wax.

11. The field test kit of claim 1 wherein the means of providing heat to the reaction chamber is nichrome wire wrapped around the reaction chamber which is connected to a battery pack through electrical wires, a switch, and a light emitting diode.

12. The closed reaction vessel of claim 5 wherein the means of providing heat is a nichrome wire wrapping.

13. The closed reaction vessel of claim 5 wherein the means of providing heat is placing the reaction vessel directly into a container of boiling water.

14. The field test kit of claim 10 wherein the wax is a low melting paraffin wax.

* * * * *